United States Patent [19]

Galante et al.

[11] Patent Number: 4,536,894
[45] Date of Patent: Aug. 27, 1985

[54] HIP PROSTHESIS WITH FLARED POROUS BONY INGROWTH PADS

[76] Inventors: Jorge O. Galante, One Brighton La., Oak Brook, Ill. 60521; William Rostoker, 2052 W. 108th Pl., Chicago, Ill. 60643

[21] Appl. No.: 520,347

[22] Filed: Aug. 4, 1983

[51] Int. Cl.³ .............................................. A61F 1/04
[52] U.S. Cl. ........................................ 623/22; 623/16; 623/18; 128/92 C; 128/92 G
[58] Field of Search .................... 3/1, 1.9, 1.91, 1.911, 3/1.912, 1.913; 128/92 C, 92 CA, 92 G

[56] References Cited

U.S. PATENT DOCUMENTS

| | | | |
|---|---|---|---|
| 3,623,164 | 11/1971 | Bokros | 3/1.9 |
| 3,906,550 | 9/1975 | Rostoker et al. | 3/1.912 |
| 3,992,725 | 11/1976 | Homsy | 3/1 |
| 4,202,055 | 5/1980 | Reiner et al. | 3/1.51 |

FOREIGN PATENT DOCUMENTS

| | | | |
|---|---|---|---|
| 0038902 | 3/1982 | European Pat. Off. | |
| 2400134 | 7/1974 | Fed. Rep. of Germany | 3/1.9 |
| 1554454 | 10/1979 | United Kingdom | |

Primary Examiner—Richard J. Apley
Assistant Examiner—David Isabella
Attorney, Agent, or Firm—Sherman & Shalloway

[57] ABSTRACT

A femoral hip prosthesis is provided with porous bony ingrowth material on each of the anterior and posterior sides. The bone ingrowth materials on each side flare or expand outwardly in the proximal direction with respect to the sides of the prosthesis, to provide a wedge shaped configuration of at least 1 millimeter increase in thickness at the upper proximal end of the porous materials from the point where the expansion begins. By impacting the prosthesis in the surgically prepared opening in the femoral canal a wedge tight fitting is achieved to assure initial stabilization of the prosthesis for a sufficiently long period of time, e.g. about six weeks or more, until bony ingrowth into the porous materials has occurred to provide long term stabilization. The distal end of the stem of the prosthesis is chamfered anteriorly and posteriorly so that the prosthesis can be used for either the right leg femur or left leg femur without impinging on the anterior bow.

13 Claims, 8 Drawing Figures

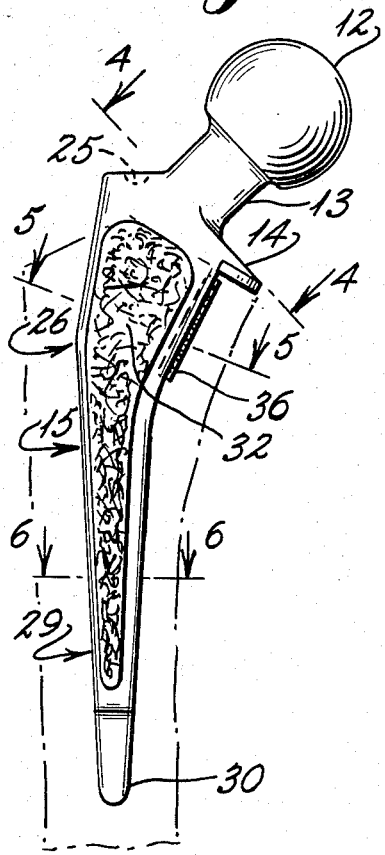
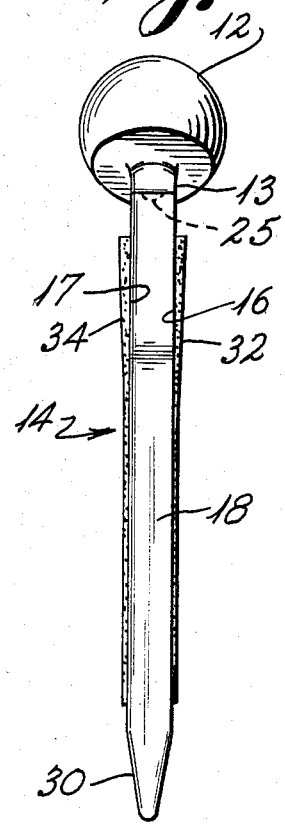
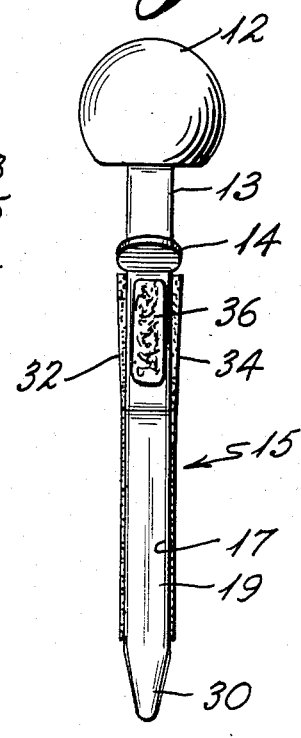
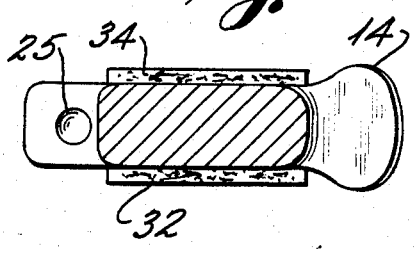
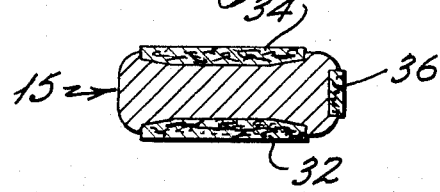
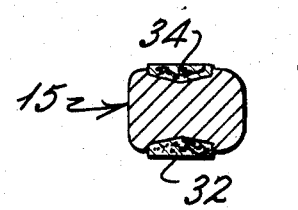

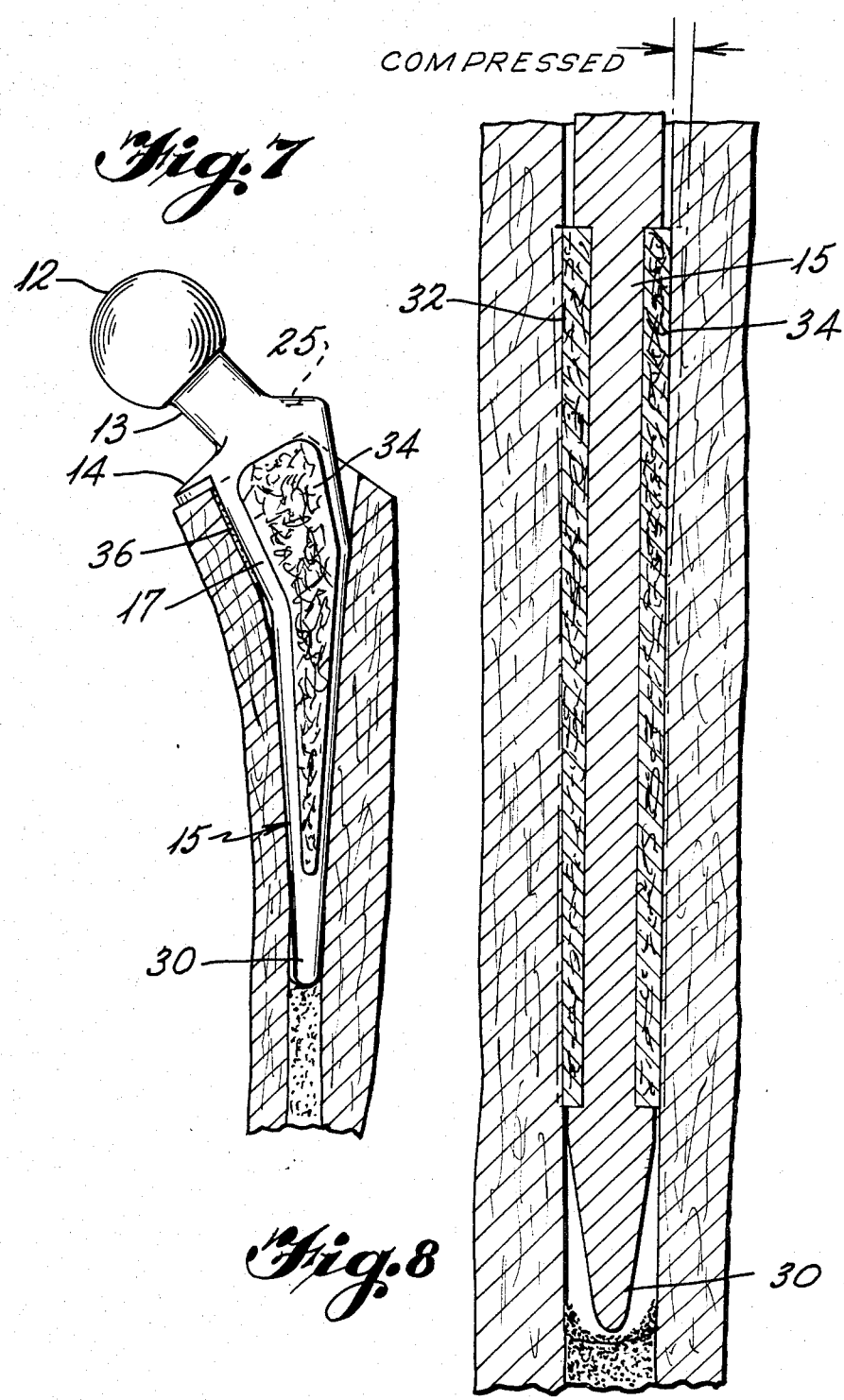

HIP PROSTHESIS WITH FLARED POROUS BONY INGROWTH PADS

BACKGROUND OF THE INVENTION

1. Field of the Invention

This invention relates to a femur prosthetic device. More particularly, this invention relates to a hip prosthesis adapted for insertion into the upper medullary canal in the femur of a patient. The hip prosthesis of this invention is of the type generally characterized as including a head or ball member, a shaft or stem member for insertion into the intermedullary canal, and a neck member connecting the head and stem, and also including at least one porous metal surface portion which provides for stabilization by bone ingrowth without requiring any cement.

2. Description of the Prior Art

Hip prostheses are known in the art and these have included various design configurations of the various components, including the head member, neck, collar and stem. Several of these prosthetic devices have been provided with porous surfaces for bone ingrowth. Representative of patents in this field include U.S. Pat. No. 3,906,440 to W. Rostoker and J. Galante, British Patent Specification 1,554,454 to J. C. Bokros, and European Patent No. EPO 038,902 A3 to Gebruder Sulzer Aktiengeseellschaft (Sulzer).

Nevertheless, further improvements in the total design of hip prostheses are required to assure stable fixation of the implanted prosthesis at the bone/metal interface. Thus, in cemented prosthetic devices, there has not been satisfactory fixation due to the various stress loads, i.e. the compression, shear and torsion to which the implanted device is subjected. These mechanical forces, especially shear and torsion, weaken the bone cement bond. In addition, it is known that there is a tendency for bone resorption which also weakens the cement bond between the bone, e.g. intramedullary canal of the femur and the femoral prosthesis.

On the other hand, by providing a bond ingrowth surface on the prosthetic device, a more stable fixation would be expected and some advances along these lines have been made. However, even with prosthetic devices provided with a bone ingrowth surface or surfaces, sufficient bone ingrowth to provide long term stabilization requires the prosthesis to be stably fixed without movement for at least 6 weeks, and any relative motion of the prosthesis during that period prevents or minimizes bony ingrowth. This is a particularly significant problem in view of the difficulty in fitting the prosthesis with sufficiently close tolerances to provide large contact areas between the porous material and the bone, even where the entire outer surface of the prosthesis is fabricated from porous material.

As a result, an incidence of 10 to 20% of femoral stem loosening or failure in total hip arthoplasty patients followed over 5 or more years, especially in younger patients, has been reported.

SUMMARY OF THE INVENTION

Accordingly, it is an object of this invention to provide a femoral hip prosthesis which avoids these problems of prior art devices.

A particular object of the invention is to provide a femoral hip prosthesis which combines long term stabilization by bone ingrowth with initial stable fixation being provided by the configuration of the prosthesis and the porous bony ingrowth members.

A further object of the invention is to provide a hip prosthesis in which initial stabilization is obtained by porous bony ingrowth members of relatively low compression modulus provided on each of the anterior and posterior sides of the prosthesis and which flare outwardly from the exterior surface of the sides of the prosthesis to provide a wedged shape configuration whereby the prosthesis can be tightly wedged into the upper end of the femur to provide initial stabilization without damage to the bone while the distal end of the shaft is substantially straight from front to back and side to side and is chamfered anteriorly and posteriorly so that a single hip prosthesis can be used for either the right or left side without impinging on the anterior bow of the femur.

A still further object of the invention is to provide an improved method for placing a femoral insert into the intermedullary canal wherein the dimension at the upper end of the hollowed out portion of the femoral canal is made slightly less than the thickness of the maximum thickness between the wedge shaped porous ingrowth members so that upon insertion of the prosthesis into the femoral canal, the porous ingrowth members are compressed and a tight fit is obtained to provide initial stabilization of the inserted prosthesis.

These and other objects of the present invention which will become more apparent from the following description are generally accomplished by an improved femoral insert for hip joint prosthesis of the type having a generally spherical shaped head member, a neck member connected to the head member and a stem or shaft member having a proximal portion connected to the neck member and a distal portion wherein each of the anterior and posterior sides of the stem is provided with a porous bony ingrowth member gradually increasing in thickness in the proximal direction in at least that region of the proximal portion corresponding to the metaphyseal portion of the bone, whereby the increasingly thick porous members on the anterior and posterior sides provide a wedge tight fit when inserted into the femoral canal.

Preferably, the porous bony ingrowth members extend over both the proximal portion and distal portion of the anterior and posterior sides of the stem. In one embodiment of the invention, the porous bony ingrowth members gradually increase in thickness over substantially their entire length from the distal portion to the proximal end. In a more preferred embodiment, the porous members have a relatively constant thickness in the regions distal to the metaphyseal portion of the bone and flare outwardly in the proximal portion of the anterior and posterior sides corresponding to the metaphyseal portion of the bone, which is generally in the proximal 3 cm to 4 cm of the porous members.

In another aspect of the invention, an improved method is provided for cementless insertion of a femoral hip joint prosthetic device in a surgically prepared opening in the femoral canal whereby long term stabilization of the insert is obtained by providing the stem of the insert with a porous bony ingrowth member on each of the anterior side and posterior side, each of the porous ingrowth members gradually increasing in thickness in the proximal direction in at least that region of the proximal portion of the stem which corresponds to the metaphyseal portion of the bone, whereby the increasingly thick porous ingrowth members on the anterior and posterior sides provide a wedge shaped cross-section; and fitting the femoral insert into the surgically prepared opening in the femoral canal whereby the wedge shaped porous ingrowth members are force fitted into the femoral canal to provide for initial stabilization of the femoral insert.

The invention will now be described in greater detail by way of specific embodiments and with the aid of the accompanying drawings in which:

BRIEF DESCRIPTION OF THE DRAWINGS

FIG. 1 is a front elevation view of an embodiment of the hip prosthesis;

FIG. 2 is a left side elevation view of the hip prosthesis shown in FIG. 1;

FIG. 3 is a right side elevation view of the hip prosthesis shown in FIG. 1;

FIG. 4 is a cross-section view along the lines 4—4 in FIG. 1;

FIG. 5 is a cross-section view along the lines 5—5 in FIG. 1;

FIG. 6 is a cross-section view along the lines 6—6 in FIG. 1;

FIG. 7 is an elevation view showing the prosthetic device of FIG. 1 inserted into a femur which is shown in cross-section; and FIG. 8 is an enlarged side sectional view of a portion of FIG. 7, showing the stem and porous bony ingrowth pads impacted into the intermedullary canal of the femur.

DETAILED DESCRIPTION OF THE INVENTION

The femoral prosthesis is shown generally at 10 in FIGS. 1-3. The prosthetic device includes spherical head member 12, neck member 13, collar 14 and the shaft or stem member 15. The prosthetic device is preferably fabricated from titanium metal or titanium alloy, but any other biologically compatible, inert metal that has sufficient mechanical strength can be used. Head 12 is generally globular in shape and assumes somewhat more than a hemisphere. The head member has a highly polished bearing surface to mate with the hip socket, which may be the natural hip socket or an artificial prosthesis in the case of total hip replacement. The neck member 13 connects the head member 12 to the stem 15 and is preferably generally rectangular in cross section with the shorter dimension being in the anterior to posterior direction, i.e. from front to back.

Collar 14 extends medially from the stem at the juncture with the neck and has an arcuate elliptical periphery which bulges slightly with respect to the left and right lateral sides of the stem 15. The extended collar rests on the upper surface of the femoral shaft bone, i.e. the cut surface of the calcar, as best seen in FIG. 7, to provide for medial load transfer and stabilization of the implanted prosthesis. Furthermore, since the collar is not present on the front or back sides of the prosthesis, the procedure for removing the implanted device, when and if necessary, becomes greatly simplified. Thus, after bone ingrowth into the porous ingrowth surface as discussed more fully below, it is possible to extract the prosthesis by inserting an appropriate cutting tool, for example, an osteotome, which can be introduced proximally along the sides of the prosthesis to sever the bony ingrowth attachment. In addition, it would be possible using a device such as the Midas Rex cutting tool to cut the collar at the juncture with the side wall of the stem and then introduce the osteotome anteriorly to sever whatever remaining attachments might exist in that region. While the presence and length of the collar provide for immediate and satisfactory stability of the implanted prosthesis, the principal means for providing for the initial short term stabilization is achieved, in accordance with the present invention, by the configuration of the stem and especially by the provision of the porous bony ingrowth materials provided on the anterior and posterior lateral sides of the stem which are constructed so as to obtain a tight fit of the prosthesis in the intermedullary canal by virtue of being raised with respect to the solid surfaces of the prosthesis.

Stem 15 is formed with substantially flat front (anterior) 16 and back (posterior) 17 side walls which are joined by a convex (left as viewed in FIG. 1) lateral side wall 18 and a concave lateral side wall 19. Side wall 18 includes upper and lower portions which are also flat and which form an angle which, as shown in FIG. 1 is about 12° but which can generally range from about 8° to about 20°. On the other hand, the generally straight lateral surfaces of the concave side are joined by a smooth transitional curved portion.

The upper wall portions of the left and right lateral side walls, together with the corresponding upper portions of the front and back side walls can be considered as forming the upper or proximal portion 26 of stem 15, while conversely the lower wall portions of the left and right lateral side walls, together with the corresponding lower portions of the front and back side walls, can be considered as forming the lower or distal portion 29 of stem 15. The upper proximal portion 26 of stem 15 is broad in the medial-lateral direction with the greatest width occurring at the uppermost proximal end at the juncture with collar 14 and gradually decreases in width to the juncture with the distal portion 29. Similarly, the distal portion of stem 15 gradually tapers in the medial-lateral direction from the juncture with the proximal portion to the distal or free end 30.

Furthermore, as best seen in FIGS. 2 and 3, the side walls 18, 19 are substantially uniform in width over their length except that the tip 30 of the shaft member is chamfered anteriorly and posteriorly. Accordingly, the prosthetic device of this invention has the advantage that it can be used for either the right femur or left femur and further, the chamfered tip of the prosthesis prevents the shaft from impinging on the anterior bow of the femur as can be seen in FIGS. 7 and 8.

The prosthetic device 10 is provided on its front (anterior) side wall 16 and on its rear (posterior) side wall 17 with porous bony ingrowth members 32, 34, respectively and these are preferably provided in the form of prefabricated porous pads which may be secured directly to the flat surfaces of walls 16, 17, but preferably are pressed into hollow depressions (shown in FIGS. 5 and 6) provided for this purpose in each of the front and rear side walls of the stem, and are then subjected to sintering to securely adhere the porous pads to the sides of the stem. According to this invention, the porous pads 32, 34 project beyond the external surface of walls 16, 17 and gradually increase in thickness at least in that region of the proximal portion corresponding to the metaphyseal portion of the bone. Accordingly, the anterior and posterior porous bony ingrowth members protrude beyond the side walls 16, 17 and additionally flare or expand outwardly with respect to the external surfaces of side walls 16, 17 to create a wedging, very tight fit when the prosthesis is inserted into the intermedullary canal. Preferably the pads flare only in the region corresponding to the metaphyseal portion of the bone which corresponds to the proximal or upper 3 to 4 cm of the porous material. In the remaining diaphyseal portion (distal area of the porous members), the porous members may still extend outwardly of the stem but preferably are of a uniform thickness. However, it is also possible for the porous bony ingrowth members to continuously increase in thickness from the distal end to the proximal end. In practice, there is at least about 1 millimeter difference in thickness on each pad from where the pad begins to flare outwardly from the external surface of side walls 16, 17 to the proximal end of the pad, although the difference may preferably be 2 millimeters to 3 millimeters. In extreme cases, this difference may be as much as 5 millimeters or possibly even as high as 7 millimeters in thickness on each side from the beginning to the end of the flare. Although in the embodiment of the invention illustrated in the figures, the portion of the pad in the distal portion of the stem protrudes from the anterior and posterior surfaces, for example by about one-half millimeter, it is also within the scope of the invention for the porous material in the distal portion to be flush with the anterior or posterior side walls. It can, therefore, be appreciated that the prosthetic device of the present invention provides for initial stabilization by virtue of the collar 14, by the medial/lateral wedge shape of the proximal portion 26 of the stem, and especially by the anterior and posterior porous bony ingrowth members which flare or expand outwardly to create a very tight wedge fit when inserted in the intermedullary canal. In this manner, stabilization of the prosthesis for sufficient time to permit the bone to grow into and throughout the interstices of the porous bony ingrowth members in order to achieve long term stabilization is assured.

In accordance with a preferred embodiment of the invention, still further assurance of long term stabilization can be achieved by providing an additional porous bony ingrowth member 36 on the concave side wall of the prosthesis in the area of the calcar. Here too, there is a stand-off of the porous member 36 with respect to the surface of lateral side wall 19 so that, as shown in FIG. 7, it is the porous member which comes into contact with the surrounding bone. However, in this case, the porous member 36 can have a uniform thickness over its entire length, or it may also be flared. A substantially uniform thickness in the range of from about 0.5 to 3 millimeters is preferred. Still further, if desired, additional areas for bony ingrowth can be provided on the convex side wall of the stem.

Any fiber or powdery porous bony ingrowth materials which have a compression modulus comparable to that of the femoral bone can be used in the present invention. If the compression modulus of the porous material is much greater than that of the bone on which it is impacted, there is a substantial risk that the pressure exerted on the bone by the wedge shaped porous members could cause the bone to split or crack or promote bone resorption. Generally, metallic fibers are preferred, although inorganic, ceramic, and even synthetic organic polymeric fibers may also be used. For example, typical fibrous porous bony ingrowth materials are described in U.S. Pat. No. 3,992,725 to Homsy, and U.S. Pat. No. 3,906,550 to Rostoker and Galante. Sintered ceramic or metal powder porous bony ingrowth materials generally have a compression modulus substantially in excess of $10^6$ psi and cannot be used in this invention. The materials previously disclosed in the Rostoker and Galante patent 3,906,550 are especially preferred for use in the present invention and the disclosure of said patent is specifically incorporated herein by reference. The sintered titanium wire materials of Rostoker and Galante are especially preferred since, by modifying the porosity, wire density, wire diameter, etc., they can be fabricated with varying degrees of compressibility greater than the compressibility of bone and preferably with a compression modulus in the range of from about 50,000 to about 500,000 psi, more preferably from about 100,000 to 300,000 psi. Since the compressibility of the wedge shaped porous members is comparable to that of the bone, even though the opening in the intermedullary canal is reamed to a dimension slightly less than the maximum thickness between the outer surfaces of the porous pads in their uncompressed state, the pads will be slightly compressed upon insertion into the femur, (see FIG. 8) and the forces of contact between the porous members of the prosthesis and the bone will be distributed over a relatively large area, thereby avoiding damage to the bone. Thus, an extremely tight and stable fitting of the prosthetic device is achieved by virtue of the positive engagement pressure between the porous pads and the bone, while at the same time contact between the hard metal surface of the prosthesis and the bone is avoided or at least minimized. The expanding wedged shape characteristic of the porous ingrowth members which provides for the ability to obtain a very tight fit at the time the prosthesis is impacted into the intermedullary canal is particularly important because following reaming, the upper end of the femur often becomes configured like a funnel and the flared configuration of the porous ingrowth material allows for intimate contact between the faces of the prosthesis and the surrounding bone to assure positive engagement pressure but in which due to the low compression modulus of the porous material, the forces are distributed over a large area. That is, the pressure developed by the wedge geometry acting on the bone is limited by the relatively low elastic or compression modulus of the porous bony ingrowth members, especially the sintered titanium wire porous material, and accordingly, the risk of splitting the bone is thereby minimized.

In practice, the shoulder of stem 15 is provided with an indentation 25 in which an appropriate tool can be fitted to assist in impacting the prosthesis into the intermedullary canal of the femur.

By changing the dimensions of the porous ingrowth members, the prosthesis can be made to fit patients with normal femoral structure and patients with osteoporosis or other deformities which result in increased dimensions in their AP diameter. Therefore, by suitable changes in thickness dimensions of the pads a large patient population can be fitted without drastically changing the appearance the prosthesis.

Still further, it is envisioned that the hip prosthesis can be stocked in several standard sizes and combinations to fit a varying patient population. These sizes can increase progressively in overall dimensions, including AP dimensions, width and length. For example, the femoral neck can be stocked in lengths of 28 mm, 30 mm, 34 mm and 40 mm, measured from the base of the collar to the center of the spherical head. Standard sizes for the length of the stem measured from the base of the collar to the free distal end can typically be 200 mm, 220 mm, 230 mm, 250 mm, 260 mm, 270 mm and 280 mm. The diameter of the spherical head can also be varied within the range of, for example, from about 20 mm to about 40 mm with a typical dimension being about 28 mm diameter.

What is claimed is:

1. In a femoral insert for hip joint prothesis having a generally spherical shaped head member, a neck member connected to the head member and a stem having a proximal portion connected to the head member and a distal portion, the improvement comprising:

said stem having substantially flat anterior and posterior sides, each said side having a hollow depression therein, and on each of the anterior and posterior sides of said stem, a porous body ingrowth member extending from said hollow depression over at least that region of the proximal portion corresponding to the metaphyseal portion of the bone, each of said porous members gradually increasing in thickness and protruding increasingly further out of its respective hollow depression in the proximal direction, whereby said increasingly thick porous members on said anterior and posterior sides provide a wedge tight fit when inserted in the femoral canal.

2. The femoral insert of claim 1 wherein said porous bony ingrowth members extend over both the proximal portion and distal portion of the anterior and posterior sides.

3. The femoral insert of claim 2 wherein the porous members have a relatively constant thickness in the regions distal to the metaphyseal portion of the bone.

4. The femoral insert of claim 3 wherein there is at least a 1 millimeter difference in thickness in each of the porous members from where the porous members begin to increase in thickness to the proximal ends of the porous members.

5. The femoral insert of claim 3 wherein there is a difference in thickness in each of the porous members of from about 2 to 7 millimeters from where the porous members begin to increase in thickness to the proximal ends of the porous members.

6. The femoral insert of claim 5 wherein the difference in thickness ranges from about 3 to 5 millimeters.

7. The femoral insert of claim 2 wherein each of the porous members gradually increase in thickness from their distal portions to their proximal ends.

8. The femoral insert of claim 7 wherein the increase in thickness of each of the porous members from where the porous members begin to increase in thickness to the proximal end of the porous member is at least 1 millimeter.

9. The femoral insert of claim 8 wherein the increase in thickness is from about 2 to 7 millimeters.

10. The femoral insert of claim 1 which further comprises at least one porous bony ingrowth member attached to and extending from the lateral side of said stem so as to come into contact with the calcar area when the insert is fitted into the femoral canal.

11. The femoral insert of claim 1 wherein the distal end of the stem is chamfered anteriorly and posteriorly whereby the femoral insert may be used for either right side or left side hip joints without impinging on the femoral bow of the femur.

12. In a method for cementless insertion of a femoral insert hip joint prostheses in a surgically prepared opening in the femoral canal whereby long term stabilization of the insert is obtained by providing a porous bony ingrowth surface on at least one region of the stem of the femoral insert, the improvement comprising:

providing said stem with substantially flat anterior and posterior sides, each said side having a hollow depression therein, providing the insert with a porous bony ingrowth member in the anterior side and posterior side hollow depressions, each of said porous ingrowth members gradually increasing in thickness and protruding increasingly further out of its respective hollow depression in the proximal direction in at least that region of the proximal portion of the stem which corresponds to the metaphyseal portion of the bone, whereby said increasingly thick porous ingrowth members on said anterior and posterior sides provide a wedge shaped cross-section; and fitting the femoral insert into the surgically prepared opening in the femoral canal whereby the wedge-shaped porous ingrowth members are force fitted into the femoral canal to provide for initial stabilization of said femoral insert.

13. The femoral insert of claim 1, wherein said porous members are compressible.

* * * * *